US005279385A

United States Patent [19]

Riches et al.

[11] Patent Number: 5,279,385

[45] Date of Patent: Jan. 18, 1994

[54] FALL-ARREST APPARATUS

[75] Inventors: David Riches, Bangor; Leonard J. Feathers, Ty Croes, both of United Kingdom

[73] Assignee: Barrow Hepburn Sala Ltd., Portishead, England

[21] Appl. No.: 966,143

[22] PCT Filed: May 20, 1992

[86] PCT No.: PCT/GB92/00916

§ 371 Date: Jan. 21, 1993

§ 102(e) Date: Jan. 21, 1993

[87] PCT Pub. No.: WO92/20407

PCT Pub. Date: Nov. 26, 1992

[30] Foreign Application Priority Data

May 21, 1991 [GB] United Kingdom ................ 9110900

[51] Int. Cl.[5] ........................................ A61B 35/04

[52] U.S. Cl. ........................................ 182/3; 182/36

[58] Field of Search ............... 182/3, 36, 45; 248/237; 104/115

[56] References Cited

U.S. PATENT DOCUMENTS 4,674,596 6/1987 Weiner et al. .......................... 182/3
4,721,182 1/1988 Brakmann et al. .................... 182/36
4,790,410 12/1988 Sharp et al. ........................ 182/124

*Primary Examiner*—Alvin C. Chin-Shue
*Attorney, Agent, or Firm*—Dennison, Meserole, Pollack & Scheiner

[57] ABSTRACT

The invention relates to a safety apparatus comprising a safety track. A component with a lanyard attached thereto is slidable along the safety track. The sliding component comprising a tube with a longitudinal slot which allows the tube to travel past the track support.

16 Claims, 6 Drawing Sheets

FALL-ARREST APPARATUS

This invention relates to safety apparatus comprising a support for locally supporting a safety track in spaced relation to a fixture and a component to which a load can be coupled and which is displaceable along a said track.

Apparatus of this kind is useful for example in fall-arrest safety installations for protecting personnel working at height. A worker's safety belt or harness can be attached via a lanyard to the load coupling component. Movements of the worker generally parallel with the safety track, e.g a track formed by a wire cable, are unrestrained because the coupling means slides freely along the cable in response to a pull on the lanyard. And the worker is free to move away from the cable to an extent permitted by the length of the lanyard. But the coupling means remains permanently coupled with the safety track so that the installation prevents or restricts any fall of the worker.

It is important that movement of the coupling means along the safety track is not interrupted or impeded by any local track support. Usually it is necessary for there to be a plurality of such supports located at intervals along the track.

Various designs of apparatus which permit such movement of a load coupling means past local track supports are known. United Kingdom Patent No 2199880 describes a relatively simple apparatus in which a local track support has a head portion through which a wire cable can be threaded and the load coupling component comprises a longitudinally slotted tube for threading onto such cable. The bore of the tube is large enough to allow passage of the head portion of the track support and the tube slot is wide enough to allow passage of a portion of the track support adjoining that head portion. The slotted tube has profiled ends. If one of such ends strikes against the said head-adjoining portion of the track support during displacement of the coupling component along the safety track, the tube is thereby caused to rotate into a position in which that adjoining portion of the track support can pass along the slot. The said United Kingdom Patent also describes an alternative arrangement wherein a said slotted tube forms part of the local track support. In that case the load connecting means has a head portion which can slide along a said track and pass through the bore of the slotted tube, and a load attachment arm which projects from that head portion and can pass along the tube slot.

Research has been carried out into the design and performance of such a slotted tube type of apparatus with a view to combining high safety standards with improved versatility of use. The present invention results from this research.

According to the present invention there is provided apparatus comprising (i) a safety track support for locally supporting a safety rack in spaced relation to a fixture, said support having a track-locating head portion through which a said track can extend, and (ii) a load coupling component comprising a tube which can slide along a said track and means whereby a load can be attached to such tube; said tube defining a passageway along which the head portion of said track support can pass and which is peripherally interrupted by a slot for the simultaneous passage of a portion (hereafter called "neck") of the track support adjoining its said head portion; and at least one end of said tube having cam edges or faces shaped so that axial abutment pressure of said neck against a said edge or face causes a rotational movement of the tube which allows passage of said neck along the slot; characterised in that said load attachment means is connected to the tube so that such means is free to pivot relative to said tube about an axis which is parallel with and radially spaced from the axis of said tube, the pivot axis being located at a position which in end aspect of the tube is angularly offset, around the tube axis, from the ends of the tube slot and from the portion of the tube wall which is directly opposite such slot ends.

Otherwise defined, apparatus according to the invention is characterised in that the load attachment means is freely pivotable, relative to the slotted tube, about an axis which is parallel with and radially spaced from the axis of said tube, the pivot axis being located so that if the coupling component is located on a taut horizontal wire cable about which the tube is free to turn and a direct downward force is exerted on the load attachment means, the slot then lies or at least the ends of the slot then lie generally to one side of the cable. The risk of such a cable being forced into the slot under a fall-arrest load and of the tube being consequently deformed and wrenched free of the cable is thereby avoided.

Because of the aforesaid advantage, there is no necessity for the slot to follow a curved, e.g. sinusoidal path along the tube in order to ensure that in the event that the coupling component becomes subjected to a fall-arrest load, a solid, i.e. unslotted portion of the tube wall, will bear downwardly on the safety track. While the provision of a curved slot is not excluded from the scope of the invention, it is much preferred for the slot to be a straight slot in the sense that it allows the tube to travel past the track support without necessarily undergoing any turning motion around the track. Such a straight slot does not limit the permissible dimension of the track support neck, parallel with the track. Preferably the slot has, over a medial region of its length, side boundaries which are parallel with the axis of the tube, and has end portions which widen from that medial region towards the opposed ends of the tube.

Another advantage afforded by the invention is that smooth passage of the load coupling component past the track support, which is an important safety factor, is not dependent or is less dependent on the angular orientation of the load attachment means in planes normal to the direction of travel of the coupling component along the track.

Apparatus according to the invention also affords the advantage that the load coupling component is potentially versatile in that (as will be illustrated later in this specification) it is compatible with installation of a safety track at various levels, both above and below that at which pulling forces which draw the load coupling component along the safety track are applied to a lanyard or other flexible tie member connected to that load coupling component.

Apparatus according to the invention is particularly suitable for use in a personnel safety system wherein the load coupling component is attached to a worker's safety harness by means of a lanyard which is short enough to preclude any substantial amount of slack to occur in the lanyard during normal movements of a worker along a given pathway.

The foregoing advantages are attributable to the specified pivotal connection of the load attachment means to the slotted tube and to the specified location of the pivot axis relative to the tube slot.

The pivotal connection between the slotted tube and the load attachment means allows turning motion of the slotted tube around a safety track to take place, for passing a track support, without hindrance, or with less hindrance, such as may be due to some degree of tension in a lanyard connected to said attachment means.

The location of the pivotal axis in relation to the tube slot and the distribution of material in the load coupling component is preferably such that when the component is allowed to rest on a taut horizontal cable which passes through the tube and about which the tube is free to rotate, the component naturally assumes under its own weight bias an angular orientation such that at least the opposed end portions of the slot lie or extend over the top portion of the cable.

In general, it is recommended that the pivot axis in the load coupling component be located at a position which (in end aspect of the tube) is angularly spaced by between 80° and 110° around the axis of the tube from a point representing the centre of a straight path along the slot.

A suitable pivot joint, which affords negligible resistance to pivotal movement yet which is strong enough to withstand very high tensile loads, can easily be formed. There is no need for precision engineering in order to eliminate play at the joint. By contrast, in apparatus as illustrated in UK patent 2 199 880 wherein the slotted tube is rotatable in a sleeve bearing on the load attachment member, the bearing has to be accurately formed. Any significant play in the sleeve bearing could possibly result in binding of the tube when pulling forces are exerted on the load attachment member at an angle to the direction of required movement of the coupling component along the safety track.

The pivot joint between the slotted tube and the load attachment means is preferably arranged so that the bore of said tube is entirely unobstructed by any portion of that attachment means. It is preferable for the pivot axis to be within the thickness of the wall of the slotted tube. The tube and load attachment means may for example be connected by a pivot pin traversing an opening or recess in that wall. A very strong pivot joint can be effected in that manner.

In order to avoid making the slotted tube component unnecessarily heavy, it is advantageous for its wall thickness, measured in planes normal to its axis, to increase in directions away from the slot so that the region of maximum wall thickness is at a medial region, opposite the slot. This design feature can in itself give the component an inherent weight bias such that in the natural lie of the component the slotted portion of the tube is uppermost as hereinbefore referred to. In addition, the said design feature has the merit that a tube wall thickness which is considered adequate for the purpose of the pivot joint can be provided at the region of that joint without the weight penalty which would result from making the entire tube wall of that thickness.

It will normally be necessary for the load-coupling component to be capable of passing the track support in either direction of travel of the load-coupling component along the safety track. For that purpose each end of the slotted tube has to be shaped to provide cam faces or edges so that axial abutment pressure against any such edge or face causes the required rotary motion of the tube.

At the or each end of the tube at which said cam edges or faces are provided, such cam edges or faces preferably define at the extremity of the tube a slot entry mouth which subtends an angle of at least 90°. The wider are the slot entry mouths, the larger is the extent to which the angular orientation of the load-coupling component about the safety track can vary during movement of that component along the track, without risk of obstruction of such movement by a track support. The form of the flared end portions of the tube slot need not be such that their side boundaries (forming cam edges or faces) are symmetrically disposed with respect to a longitudinal centre line of the slot.

The requisite unimpeded travel of the load coupling component past the track support is dependent on the neck of the track support being at a suitable angle for entering the tube slot of the load coupling component as the latter is drawn along the safety track. In order to permit the above mentioned potential versatility of the load coupling component to be fully exploited, apparatus according to the invention can comprise track supports of different forms which afford different neck angles. When installing a safety system, track supports of one or another of such different forms can be selected depending on the intended level of installation of the safety track in relation to the level at which pulling forces will be applied to the distal end of the lanyard or other flexible tie member.

However, in preferred embodiments of the invention, the apparatus comprises a plurality of track supports each of which is formed so that it can be secured to a vertical or horizontal fixture surface in different orientations which afford different neck angles.

As in the case of apparatus as described in UK Patent 2199980, the slotted tube, instead of forming part of the load coupling component can form part of a safety track support and the load coupling component can have the features which in the foregoing description have been attributed to the track support.

In such alternative apparatus, the load coupling component comprises a head portion which can slide along a said track and means whereby a load can be attached to such head portion; and the track support comprises a fixing portion by which it can be secured to a fixture and a tube defining a passageway along which the head portion of said load-coupling component can pass and which is peripherally interrupted by a slot for the simultaneous passage of a head-adjoining portion of said load coupling component; and at least one end of said tube has cam edges or faces shaped so that axial abutment pressure of said head-adjoining portion of the load coupling component against any such edge or face causes a rotational movement of the tube to allow passage of that head-adjoining portion along the slot; the apparatus being characterised in that the slotted tube is connected to the said fixing portion of the track support so that it is free to pivot relative to that fixing portion about an axis which is parallel with and radially spaced from the axis of said tube, the pivot axis being located at a position which in end aspect of the tube is angularly offset, around the tube axis, from the ends of the tube slot and from the portion of the tube wall which is directly opposite such slot ends.

The invention includes apparatus according to the invention as hereinbefore referred to, in combination with a safety track (preferably a wire cable) along which the load coupling component is freely slidable. In most safety installations it will be necessary, because of the length of the safety track, to provide a plurality of track supports for mounting an intervals along the track.

Certain embodiments of the invention will now be described with reference to the accompanying drawings, in which.

Figure 10:
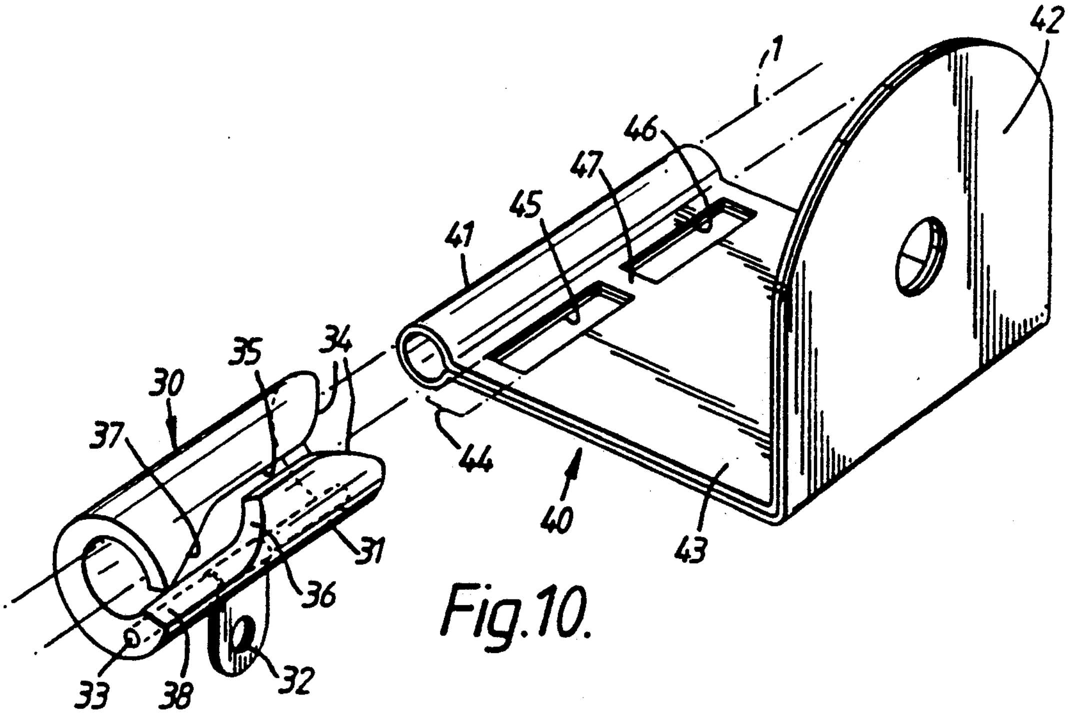
Figure 11:
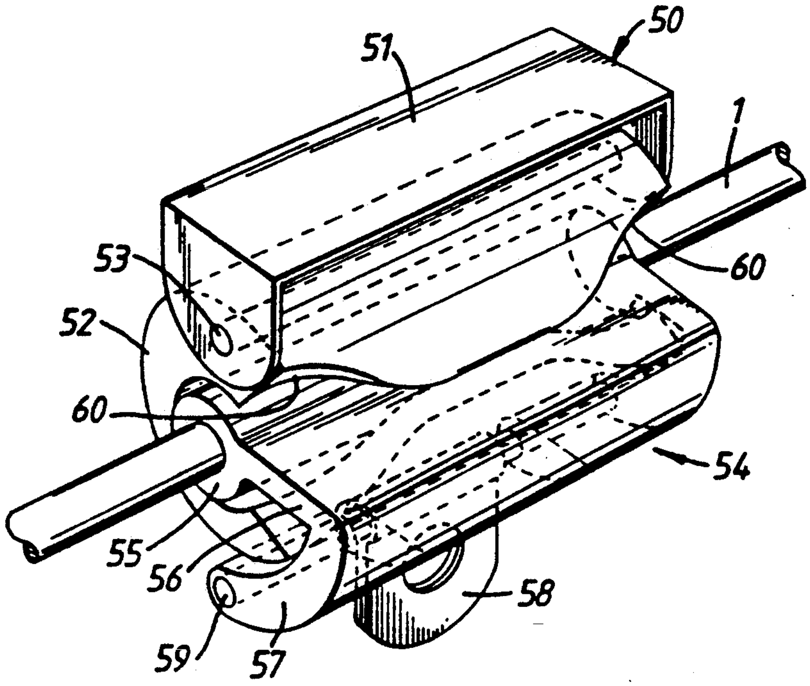
Figure 12:
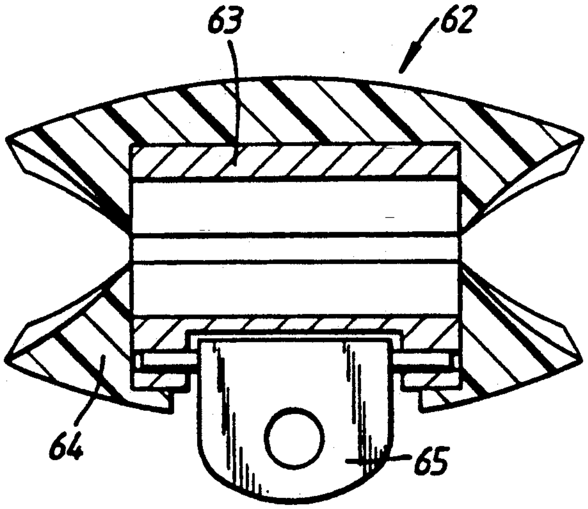

FIGS. 9*a*–9*d* 9*b* show four different simpler forms of track support bracket;

FIG. 10 is a perspective view of a load coupling component designed for unidirectional traversal of a safety track, and a co-operating track support bracket;

FIG. 11 is a perspective view of apparatus wherein the slotted tube forms part of a track support; and FIG. 12 is a sectional elevation of another construction of load coupling component.

Figure 1:
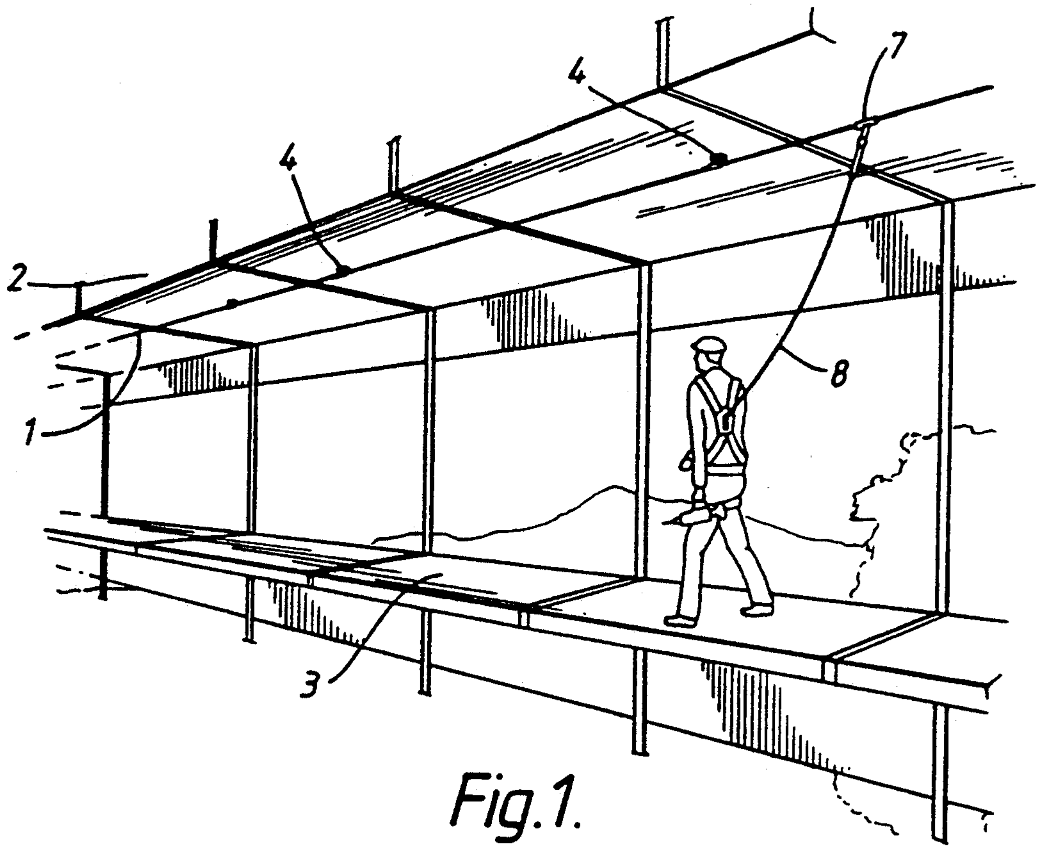
FIG. 1 shows part of a personnel fall-arrest system incorporating apparatus according to the invention.
Figure 2:
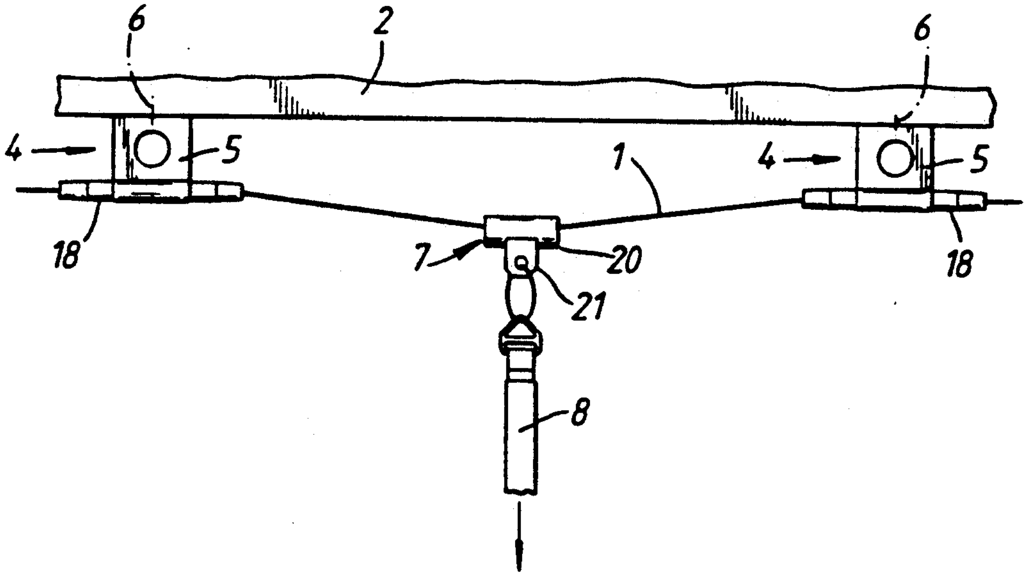
FIG. 2 shows a part of such system at the moment of a fall-arrest.

In the fall-arrest system represented in FIGS. 1 and 2, a safety track in the form of a wire cable 1 is anchored to the underside of a fixed structure 2 overhanging a worker's walkway 3. The cable can follow an endless course around that structure or it may extend between stations at which the ends of the cable are secured to the structure via suitable end fittings on the cable. Cable supports 4 are secured to the structure 2 at intervals along the course of the cable and serve to support the cable in spaced relation to that structure. Each of the supports comprises a cable-holding bracket 5 which is secured to the structure 2 by a fastening bolt 6.

A coupling component 7 is threaded onto the cable 1 and is freely slidable therealong. A worker's safety harness is connected to that coupling component via a lanyard 8. Should the worker fall, the fall-arrest loading forces are transmitted to the fixed structure via the lanyard 8, the cable 1 and the cable support brackets. The brackets can be constructed so that they have a relatively low resistance to permanent deformation such that at least the brackets which are most heavily stressed by the fall-arrest forces undergo a deformation which serves as a visual warning that the system must be thoroughly checked before it is re-used. Systems incorporating brackets with that characteristic are claimed in UK Patent Application No. 9110899.3 filed on May 21, 1991 and in International (PCT) Application No. PCT/GB91/00798 also filed on May 21, 1991.

Figure 3:
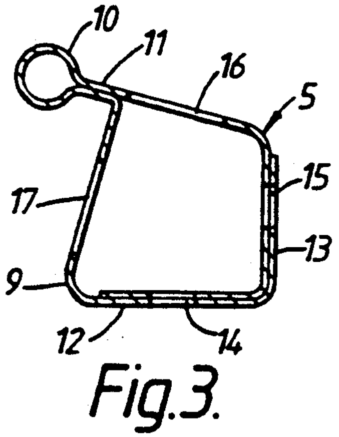
FIG. 3 is a side sectional elevation of one of the track support brackets of that system.
Figure 4:
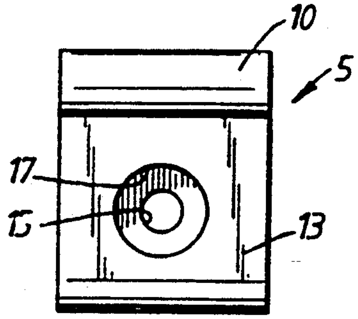
FIG. 4 is a front elevation of that bracket.
Figure 6:
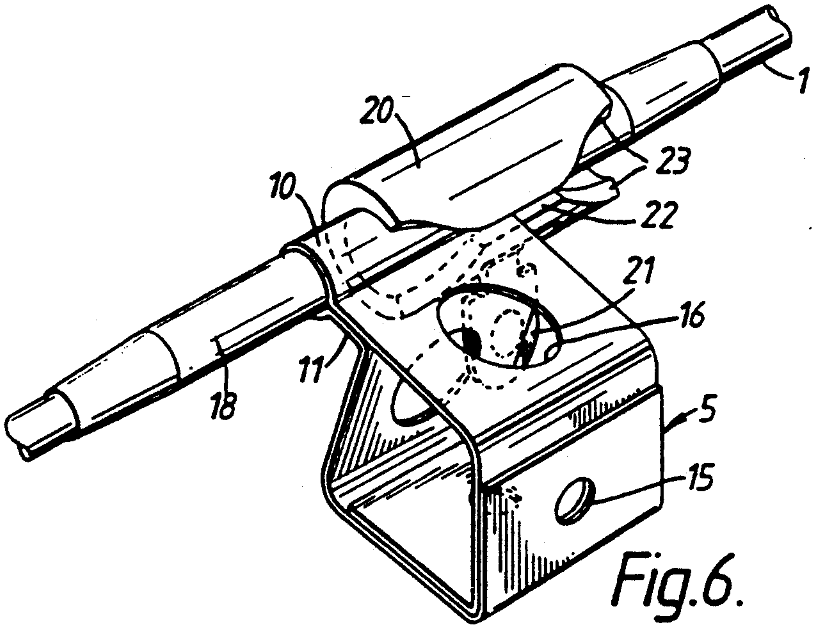
FIG. 6 shows the load coupling component in the same perspective, together with other parts of the system.

The form of the cable support brackets 5 is shown in FIGS. 3 to 4 and 6. Referring to FIGS. 3 and 4 which show the construction of the brackets in detail, each bracket has a body portion 9 in the form of a quadrilateral loop, a head portion 10 of tubular form and a neck 11 joining the head and body portions. The bracket is formed from a single strip of metal by bending the strip about transverse axes. Opposed end portions of the strip overlap to give two sides 12,13 of the quadrilateral body portion a thickness twice that of the strip. The overlapping end portions of the strip are spot-welded together in each of the sides 12,13. Holes 14,15 are formed in the body sides 12,13 respectively for the reception and location of a fastening bolt 6 (Fig. 2). When the safety system is installed, each cable support bracket is secured to the fixed structure by only one fastening bolt. The bracket can be orientated with either body side 12 or body side 13 against the fixture and it is for that reason that each of those sides is formed with a hole for the passage of such a bolt. Larger holes 16,17 are formed in the body sides opposite sides 12 and 13 to allow access of a tool to the head of the bolt.

In the installed system, the cable 1 passes through the tubular head portions 10 of the brackets 5. It is important that the cable can slide axially within the head portion of each bracket. It is beneficial to fit the tubular head portion of each bracket, as shown in FIGS. 2 and 6, with a flexible extension tube 18 which projects from each side of such head portion. It is very suitable for such extension tube to be of synthetic polymeric material, e.g. nylon. The extension tubes afford relatively low frictional restraint to sliding movement of the cable 1 and if a part of the cable between two cable support brackets is pulled downwardly by fall-arrest forces as indicated in FIG. 2, the extension tubes of those brackets serve to avoid high stress concentration on the cable due to localised bearing contact with the metal head portions of the brackets.

Figure 5:
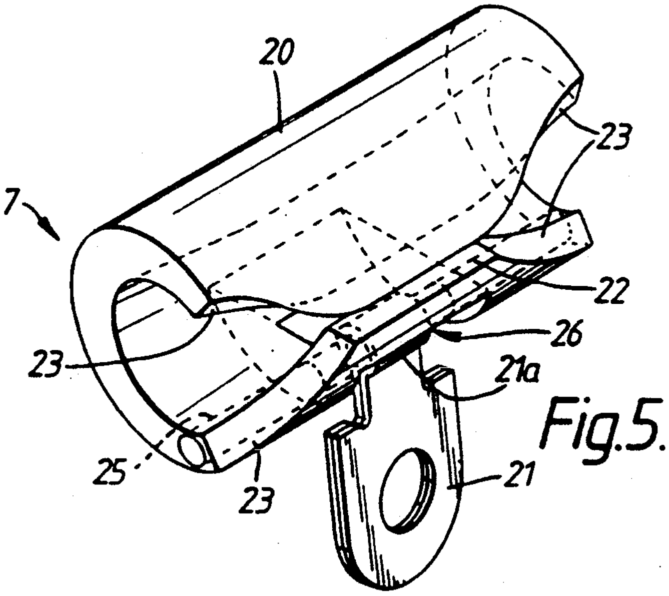
FIG. 5 is a perspective view of the load coupling component used in that system.

The coupling component 7 is best shown in FIGS. 5 and 6. The component comprises a longitudinally slotted tube 20. A link 21 for connection to the worker's lanyard 8 a shown in FIGS. 1 and 2 is pivotally connected to the wall of that tube. The bore of the tube 20 is larger than the external diameter of the tubular head portions 10 of the cable support brackets so that the slotted tube can slide over those bracket head portions. The longitudinal slot 22 has over a central portion of its length a width which is substantially smaller than the diameter of the cable 1 but is a little greater than the thickness of the neck portions 11 of the cable support brackets. The opposed end portions of the slot 22 are flared so that the mouth of the slot at each end of the tube is relatively wide. The flared portions provide cam faces or edges 23. As a worker moves along the walkway 3 (FIG. 1), the coupling component is drawn along the cable 1 by the pulling force on the lanyard 8. When the slotted tube reaches one of the cable support brackets, first the bracket extension tube 18 and then the bracket head portion 10 enters the bore of the slotted tube. The neck 11 of the bracket enters the slot 22. The coupling component therefore advances smoothly past the bracket. If the angular orientation of the slotted tube around the cable 1, at the time that tube arrives at the bracket, is not such that the central narrow portion of the slot 22 is in alignment with the neck 11 of the bracket, that neck will abut against one or another of the said cam faces or edges 23 and thereby cause the tube 20 to turn so that the coupling component continues its movement past the bracket without any impedance.

The link 21 has a sleeve portion 21*a* which is traversed by a pivot pin 25. This pivot pin bridges an opening 26 in the wall of the tube 20. The end portions of the pine are secured in receptive holes formed in that tube wall. The diameter of the pivot pin is such that it passes through the sleeve portion 21*a* of the link with clearance, so that that link is very freely pivotable relative to the slotted tube.

The pivot pin 25 is angularly spaced by 90° (around the axis of the slotted tube) from the longitudinal centre line of the slot 22.

As appears in FIG. 5, the bore of the slotted tube progressively widens towards the tube ends. This widening facilitates smooth travel of the coupling component along the cable 1 at a region (if any) where the cable undergoes a directional change, e.g. where the cable passes around a corner of the structure to which the system is secured.

The cable support brackets as shown in FIGS. 3, 4 and 6 can be used for supporting a cable or other safety track in spaced relation to a horizontal or vertical surface. And the design of the brackets is such that the orientation in which the brackets are secured to a structure can be selected in dependence on the level at which the safety track is being installed, so that the necks of the brackets are suitably disposed for entering the slot in the tube of the load coupling component as it is drawn along the cable.

Figure 7:
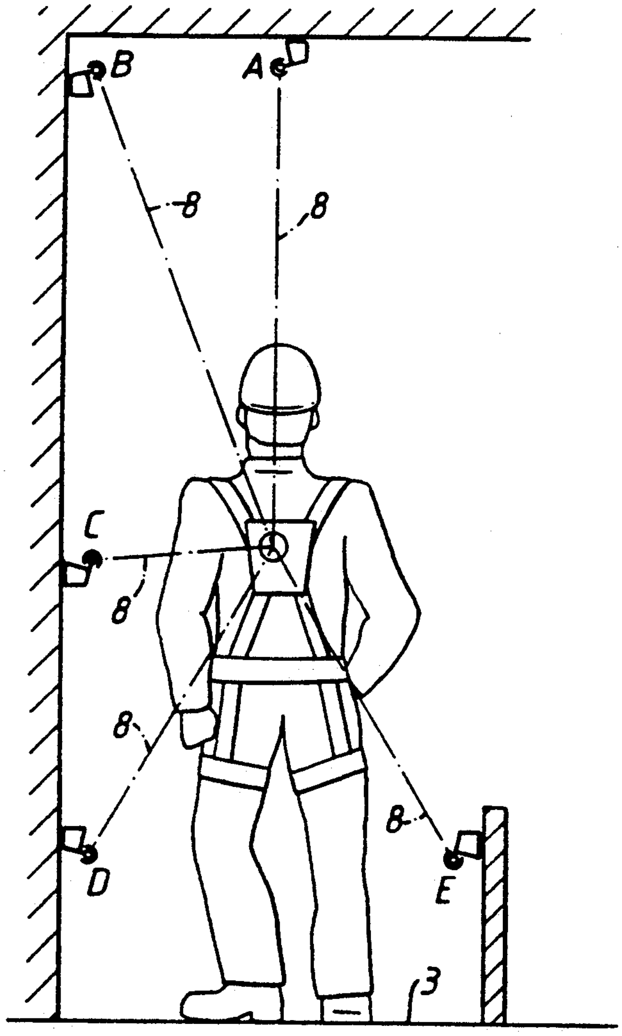
FIG. 7 shows various possible use positions of the safety track and support brackets in relation to a walkway.

FIG. 7 shows, by way of example, five possible locations A–E of a safety cable relative to a walkway 3. The orientation of the cable support brackets differs from one such location to another. The design of the brackets is such that in each of those orientations, the necks of the brackets are orientated at 15° to the horizontal or 15° to the vertical. As shown, the neck can slope upwardly or downwardly (away from the body portion of the bracket) at 15° to the horizontal or the vertical. The coupling component is compatible with the illustrated locations (and indeed with other locations) of the safety track and its supports and with the different directions in which pulling forces are exerted on the coupling component in consequence of the different track positions. This compatibility will be explained with reference to FIG. 8.

Figure 8:
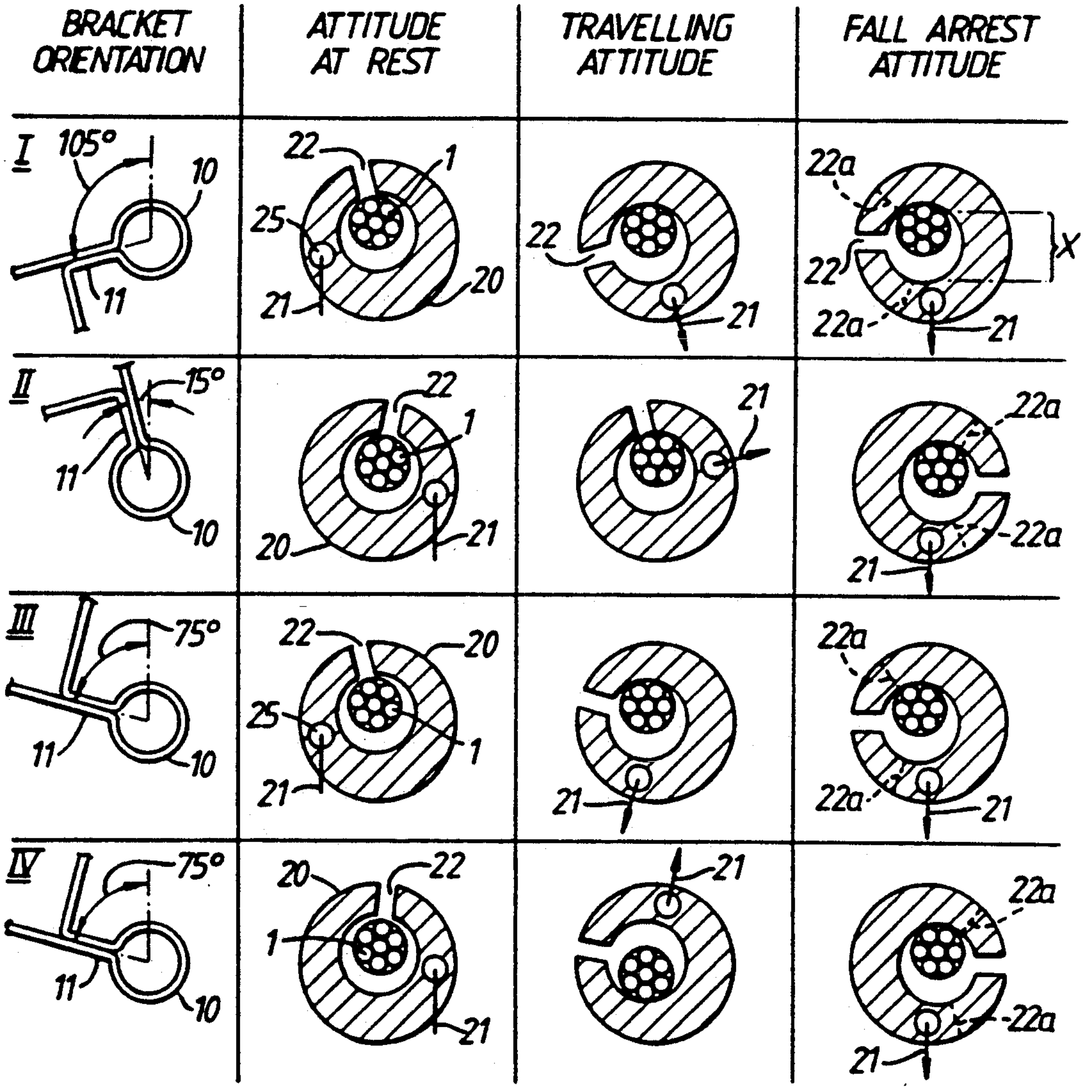
FIG. 8 is a chart of diagrams representing use of the coupling component in a variety of safety system arrangements.
Figure 9A:
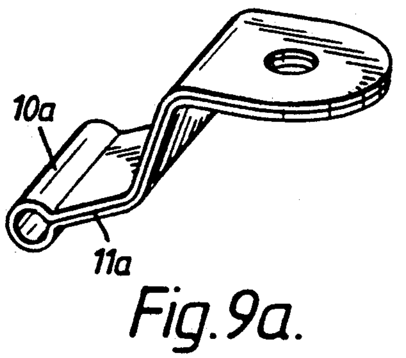
Figure 9B:
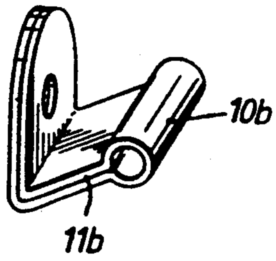
Figure 9C:
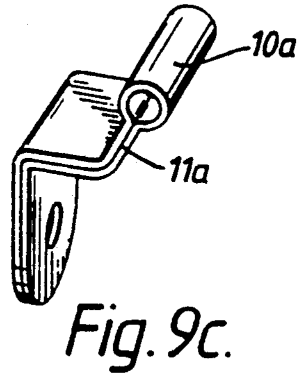
Figure 9D:
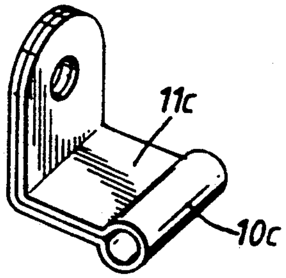

In FIG. 8, the horizontal rows of diagrams relate to four different safety system arrangements. The four arrangements, which are denoted I to IV, differ from each other in respect of the position at which the cable 1 is located in relation to the positions at which the worker's safety harness will be located during his normal movement along the walkway. As the coupling component will be attached to that harness by a lanyard, such relative positions influence the direction in which a pulling force is applied to the coupling component, causing it to be drawn along the cable, during such movements of the worker.

The first diagram (called "Bracket orientation") in each row shows the head and neck portion of one of the cable support brackets in the orientation which they have in the given safety system. Alongside that diagram in each row there are three diagrams representing three different orientations (around the cable 1) of the coupling component used in that system. Each of such diagrams shows the coupling component in transverse cross-section through the central narrow portion of the slot 22. In each diagram, the link 21 is represented merely by a line. The broken lines 22*a* in the last diagram of each row indicate the boundaries of the slot at the end of the tube. In the last diagram of the top row, the portion of the tube wall which is directly opposite the slot ends is denoted "X". It is unnecessary to identify that wall portion in more than one diagram.

The first of the three coupling component diagrams in each row shows the attitude of the slotted tube when it is at rest on the cable 1 and the worker's lanyard is in a slack condition so that the only force acting on the coupling component is the weight of the vertically suspended portion of the lanyard. In this condition of the coupling component, the slot 22 is always at the top, over the cable 1, in all of the safety system arrangements.

The second coupling component diagram in each row shows the slotted tube in the attitude (called "Travelling Attitude") which it occupies, around the cable 1, while the coupling component is being pulled along the cable by movement of the worker along the walkway 3. During that movement of the worker, unless the cable 1 is located immediately overhead with respect to the path of the worker's movement, the coupling component is subjected not only to a pulling force component acting horizontally, in the direction of its travel along the cable 1, but also to a lateral pulling force component which is directed at an angle to the vertical plane through the cable. The lateral force component causes the coupling component to assume, around the cable 1, an attitude different from that which it occupies when it is at rest. As can readily be appreciated from FIG. 7, the direction of the lateral force component depends on the level at which the safety track is disposed relative to the level of the lanyard attachment point on the worker's safety harness, and on the lateral spacing of that attachment point from a vertical plane through and parallel with the cable 1. In each of the travelling attitude diagrams in FIG. 8, the direction of the lateral force component is indicated by an arrow on the link 21 of the coupling component. It will be seen that in each of the system arrangements I to IV, the travelling attitude of the slotted tube is such that its slot 22 is appropriately positioned to allow passage of the necks 11 of the cable support brackets, which are orientated as shown in the corresponding bracket orientation diagram. Each of those diagrams shows the tube in an ideal orientation with the narrow central portion of its slot at the same angle, with respect to the vertical and horizontal planes, as the necks 11 of the cable support brackets. Because of the flaring of the end portions of the slot 2, which gives the slot relatively wide entry mouths, the actual travelling attitude of the slotted tube can differ appreciably from that ideal attitude without causing any impediment to the smooth passage of the coupling component past the brackets. Because the coupling component link 21 is pivotally connected to the slotted tube, any turning movement of the slotted tube caused by abutment of its cam edges 23 against the neck of a bracket will necessitate little if any angular displacement of the point of connection between that link and lanyard 8.

The last of the coupling component diagrams in each row in FIG. 8 shows the fall-arrest attitude of the coupling component, that is to say the attitude which it has around the cable 1, when a downward force due to a fall is exerted on the link 21. Under such a downward force, the slotted tube is caused to turn around the cable 1 into a position in which the tube slot is located to one side of the cable. There is therefore no risk of the cable being forced into the slot.

The advantage of versatile multi-positional track supports, for example as described with reference to FIGS. 3 and 4, is that a manufacturer or supplier of safety system components is relieved of the necessity to make or stock safety track supports of a variety of different designs to suit different installation conditions. However, it is to be understood that the provision of multi-positional brackets is not an essential feature of the invention in its broad aspect. The invention includes apparatus comprising a coupling component and one or more track supports having only one fastening side for securing against a fixture.

FIGS. 9*a*–9*d* show four such relatively simple track support brackets. The form of bracket shown in each of these figures is suitable for use with a coupling component as described with reference to FIGS. 5 to 8. Each of the brackets is formed from a single strip of metal by folding the strip about transverse axes. Each bracket comprises a tubular head portion for the passage of a cable and for passing through the bore of the coupling component, and a neck portion for passage along the tube slot of that component. The head portions of the brackets are designated 10*a*–19*d* respectively and the neck portions 11*a*–11*d* respectively. The bracket forms shown in FIGS. 9*a*–9*d* are respectively suitable, for example, for use at the cable locating positions A–D in FIG. 7.

FIG. 10 shows another form of coupling component and track support combination according to the invention, which is designed to permit travel of the coupling component past the track support in one direction only. The coupling component 30 comprises a slotted tube 31 and a load attachment link 32. The link 32 is pivotally connected to the slotted tube by means of a pivot pin 33 which, in end aspect of the tube, is angularly spaced, around the axis of the tube, from the edges of the tube slot. The tube slot is of bayonet type. One end portion of the slot is flared to provide a wide entry mouth, with cam edges or faces 34. Immediately behind the flared leading end portion of the slot is has a narrow portion 35. And behind that narrow portion of the slot there is a wider portion 36. At the rear end of that wider portion there is an inclined boundary edge 37. At the trailing end of the tube, that edge 37 defines with the opposite wall of the slot a narrower exit opening 38 which is angularly offset from the narrow portion 35 of the slot.

The track support 40 is in the form of a bracket comprising a tubular head portion 41, a fixing flange 42 and an arm 43 joining that flange to the head portion. The arm 43 includes a neck portion 44 adjoining the head portion. That neck portion has two aligned elongate apertures 45.46 formed therein.

When the coupling component 30, during its travel along the cable 1, reaches the support bracket 40, the leading end portion of the slotted tube passes over the head portion 41 of the bracket and the neck portion 44 of the bracket enters the narrow portion 35 of the tube slot. The advance of the coupling component continues without turning motion of the coupling component around the cable until the inclined edge 37 of the slot reaches the neck portion of the bracket. Pressure of that inclined edge against the neck portion causes the tube to turn to bring the exit opening 38 of the tube slot into registration with the neck portion 44 of the bracket. When that turning motion takes place, the portion of the tube defining the narrow portion 35 of the slot is in register with the opening 45 in the neck portion of the bracket. A portion of the wall of the slotted tube along the margin of its narrow slot portion 35 can therefore enter that opening to allow that turning movement of the tube. The movement of the coupling component can then continue past the bracket under pulling force exerted on the link 32 by the worker's lanyard. If the inclined edge 37 abuts against that bridge portion, the tube can turn as before. Once the coupling component has passed the bracket, it cannot be pulled back along the cable in the reverse direction because the trailing end of the tube is not profiled to provide cam edges or faces.

In the apparatus shown in FIG. 11, the cable 1 is supported in spaced relation to a fixture (not shown) by support brackets 50 each comprising a fixing part 51 by which the bracket can be bolted to the fixture, and a slotted tube 52. The form of the slotted tube is substantially identical with the tube 20 in FIG. 5. The tube 52 is pivotally connected to the fixing part 51 by means of a pivot pin 53 which passes, with clearance, through a passageway in the wall of the tube. The axis of the pivot joint is located so that in end aspect of the tube it is angularly offset, around the axis of the slotted tube, from the ends of the tube slot and from the portion of the tube wall which is directly opposite such slot ends.

The weight distribution of the material forming the slotted tube is such that its natural attitude at rest is that shown in the drawing, in which the tube slot opens sideways. The load coupling component 54 has a tubular head portion 55 which is slidable along the cable 1, a neck portion 56 adjoining such head portion and an underhanging claw 57. The claw defines with the neck portion a channel whose cross-sectional dimensions are sufficient to allow free passage therealong of a wall portion of the slotted tube 52 bordering its slot. A link 58 is pivotally connected to the claw 57 near its free edge. The top portion of the link defines a passageway through which a pivot pin 59 passes, with clearance. The claw has a recess formed therein, medially of its length, into which that top portion of the link intrudes. The end portions of the pivot pin are secured in the claw abreast that recess.

When the coupling component 54 is at rest on the cable 1 the pivot pin 59 is positioned directly beneath the cable 1. Consequently as the coupling component slides along the cable, its neck portion 56 is in an appropriate orientation for entering the slot in the tube 52. Depending on the angle to the vertical of any pulling force component which is exerted on the link 58 during pulling of the coupling component along the table, the neck portion 56 may then be at an inclination to the horizontal but the flaring of the end portions of the slot in the tube 52 will nevertheless allow that neck portion to enter the slot and the cam faces or edges 60 defining those flared portions of the slot ensure that the tube will automatically turn to allow the neck portion of the coupling component to pass along the narrow portion of the slot.

FIG. 12 shows a coupling component 62 which in form and function is similar to that shown in FIG. 5. However the body of the component is of composite construction. It comprises a slotted metal core 63 and a moulded plastics casing 64 in which that core is embedded. A link 65 for attachment of a load is pivotally connected to the tubular metal core. The formation of the relatively complexly shaped end portions of the coupling component by moulding enables production costs to be significantly reduced.

While the invention has been more particularly described, and is more particularly intended, for use in personnel safety systems, apparatus according to the invention can be used in systems for transporting inanimate loads while they are coupled to a safety track.

We claim:

1. Apparatus comprising (i) a safety track support for locally supporting a safety track in spaced relation to a fixture, said support having a track-locating head portion through which a said track can extend, and (ii) a load coupling component comprising a tube which can slide along a said track and means whereby a load can be attached to such tube; said tube defining a passageway along which the head portion of said track support can pass and which is peripherally interrupted by a slot for the simultaneous passage of a neck of the track support adjoining its said head portion; and at least one end of said tube having cam edges or faces shaped so that axial abutment pressure of said neck, against a said edge or face causes a rotational movement of the tube which allows passage of said neck along the slot; characterised in that said load attachment means is connected to the tube so that such means is free to pivot relative to said tube about an axis which is parallel with and radially spaced from the axis of said tube, the pivot axis being located at a position which in end aspect of the tube is angularly offset, around the tube axis, from the ends of the tube slot and from the portion of the tube wall which is directly opposite such slot ends.

2. Apparatus comprising (i) a safety track support for locally supporting a safety track in spaced relation to a fixture, said support having a track-locating head portion through which a said track can extend, and (ii) a load coupling component comprising a tube which can slide along a said track and means whereby a load can be attached to such tube; said tube defining a passageway along which the head portion of said track support can pass and which is peripherally interrupted by a slot for the simultaneous passage of a portion (hereafter called "neck") of the track support adjoining its said head portion; and at least one end of said tube having cam edges or faces shaped so that axial abutment pressure of said neck against a said edge or face causes a rotational movement of the tube which allows passage of said neck along the slot, characterised in that the said load attachment means is freely pivotable, relative to the slotted tube, about an axis which is parallel with and radially spaced from the axis of said tube, the pivot axis being located so that if a loading force is exerted on the load attachment means while the slotted tube is on a taut horizontal cable about which the slotted tube is free to turn, the tube turns under such force into a position in which the slot opens generally sideways with respect to the cable.

3. Apparatus according to claim 1 or 2, wherein the said tube slot is of a form which allows the tube (when the apparatus is in use) to travel past the track support without necessarily undergoing any turning motion around the track.

4. Apparatus according to claim 1 or 2, wherein the location of the pivotal axis in relation to the tube slot and the distribution of material in the slotted tube component is such that when the component is allowed to rest on a taut horizontal cable which passes through the tube and about which the component is freely rotatable, the component naturally assumes under its own weight bias an angular orientation such that at least the end portions of the slot lie or extend over the top portion of the cable.

5. Apparatus according to claim 4, wherein the pivot axis in the load coupling component (as viewed in end aspect of the tube) is angularly spaced by between 80° and 110° from a point representing the centre of a straight path along the slot.

6. Apparatus according to claim 5, wherein the pivotal connection between the slotted tube and the load attachment means is arranged so that the bore of said tube is entirely unobstructed by any portion of the load attachment means.

7. Apparatus according to claim 6, wherein the pivot axis is within the thickness of the wall of the slotted tube.

8. Apparatus according to claim 7, wherein pivotal connection between the slotted tube and the load attachment means is effected by means of a pivot pin which traverses an opening or recess in the wall of the slotted tube.

9. Apparatus according to claim 8, wherein the thickness of the wall of the slotted tube increases away from the slot in planes normal to the tube axis.

10. Apparatus according to claim 9, wherein the end portions of the slot are flared to form slot entry mouths each of which subtends, at the corresponding end of the tube, an angle (around the tube axis) of at least 90°.

11. Apparatus according to claim 10, in combination with a safety track (preferably a wire cable) along which the load component is freely slidable.

12. Apparatus according to claim 11, wherein there is a plurality of track supports each of which is formed so that it can be secured to a vertical or horizontal fixture surface in different orientations which afford different neck angles.

13. Apparatus according to claim 1 or 2, wherein the pivot axis in the load coupling component (as viewed in end aspect of the tube) is angularly spaced by between 80° and 110° from a point representing the centre of a straight path along the slot.

14. Apparatus according to claim 13, wherein the pivotal connection between the slotted tube and the load attachment means is arranged so that the bore of said tube is entirely unobstructed by any portion of the load attachment means.

15. Apparatus according to claim 14, wherein the pivot axis is within the thickness of the wall of the slotted tube.

16. Apparatus which comprises (i) a load coupling component having a head portion which can slide along a safety track and having means whereby a load can be attached to such head portion; and (ii) a track support having a fixing portion by which it can be secured to a fixture and a tube defining a passageway along which the head portion of said load-coupling component can pass and which is peripherally interrupted by a slot for the simultaneous passage of a head-adjoining portion of said load coupling component; and at least one end of said tube has cam edges or faces shaped so that axial abutment pressure of said head-adjoining portion of the load coupling component against any such edge or face causes a rotational movement of the tube to allow passage of that head-adjoining portin along the slot; the apparatus being characterised in that the slotted tube is connected to the said fixing portion of the track support so that it is free to pivot relative to that fixing portion about an axis which is parallel with and radially spaced from the axis of said tube, the pivot axis being located at a position which in end aspect of the tube is angularly offset, around the tube axis, from the ends of the tube slot and from the portion of the tube wall which is directly opposite such slot ends.

* * * * *

UNITED STATES PATENT AND TRADEMARK OFFICE
CERTIFICATE OF CORRECTION

PATENT NO. : 5,279,385

DATED : January 18, 1994

INVENTOR(S) : David Riches et al

It is certified that error appears in the above-identified patent and that said Letters Patent is hereby corrected as shown below:

Column 11, lines 34 and 35, "(hereafter called "Neck")" should be --neck--.

Column 12, line 58, "portin" should be --portion--.

Signed and Sealed this

Twenty-fourth Day of May, 1994

*Attest:*

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : 5,279,385

DATED : January 18, 1994

INVENTOR(S) : David Riches et al

It is certified that error appears in the above-indentified patent and that said Letters Patent is hereby corrected as shown below:

Column 11, lines 34 and 35, "portion (hereafter called "neck")" should be --neck--.

Column 12, line 58, "portin" should be --portion--.

This certificate supersedes Certificate of Correction issued May 24, 1994.

Signed and Sealed this

Twenty-eight Day of February, 1995

Attest:

BRUCE LEHMAN

*Attesting Officer*

*Commissioner of Patents and Trademarks*